(12) United States Patent
Li et al.

(10) Patent No.: US 12,156,320 B2
(45) Date of Patent: Nov. 26, 2024

(54) X-RAY MACHINE HEAD AND IMAGE DEVICE

(71) Applicant: Beijing Aili Technology Co., Ltd., Beijing (CN)

(72) Inventors: Yue Li, Beijing (CN); Zhongjun Zhang, Beijing (CN)

(73) Assignee: Beijing Aili Technology Co., Ltd., Beijing (CN)

( * ) Notice: Subject to any disclaimer, the term of this patent is extended or adjusted under 35 U.S.C. 154(b) by 487 days.

(21) Appl. No.: 17/466,629

(22) Filed: Sep. 3, 2021

(65) Prior Publication Data

US 2021/0400795 A1 Dec. 23, 2021

Related U.S. Application Data

(63) Continuation-in-part of application No. PCT/CN2020/086352, filed on Apr. 23, 2020.

(30) Foreign Application Priority Data

Mar. 6, 2019 (CN) .......................... 201910166518.5

(51) Int. Cl.
*H05G 1/08* (2006.01)
*H05G 1/06* (2006.01)
(Continued)

(52) U.S. Cl.
CPC ............... *H05G 1/085* (2013.01); *H05G 1/06* (2013.01); *H05G 1/12* (2013.01); *H05G 1/32* (2013.01); *H05G 1/34* (2013.01)

(58) Field of Classification Search
CPC ....................................................... H05G 1/085
See application file for complete search history.

(56) References Cited

U.S. PATENT DOCUMENTS

| 2014/0177805 A1* | 6/2014 | Wang ....................... H05G 1/00 378/104 |
| 2015/0078510 A1 | 3/2015 | Tang et al. |

FOREIGN PATENT DOCUMENTS

| CN | 104470176 A | 3/2015 |
| CN | 205514642 U | 8/2016 |

(Continued)

OTHER PUBLICATIONS

WIPO; Application No. PCT/CN2020/086352; International Search Report and Written Opinion mailed Aug. 3, 2020.

*Primary Examiner* — Chih-Cheng Kao
(74) *Attorney, Agent, or Firm* — Fitch, Even, Tabin & Flannery, LLP

(57) ABSTRACT

The present invention discloses an X-ray machine head and an image device, and relates to the field of X-ray image devices. The X-ray machine head comprises a high-voltage DC power supply unit, a low-voltage DC power supply unit, one or more first switch units, one or more second switch units, a central information processing unit, a housing, one or more filament power supply units, a communication unit, one or more X-ray tubes, and an insulating medium which is contained in the housing. The X-ray machine head is small in volume, which is conducive to portable applications. By directly controlling a gate of a gate-controlled X-ray tube to control the occurrence and termination of X-rays, the imaging quality is high and the radiation damage is small.

20 Claims, 6 Drawing Sheets

(51) Int. Cl.
   *H05G 1/12*  (2006.01)
   *H05G 1/32*  (2006.01)
   *H05G 1/34*  (2006.01)

(56) References Cited

FOREIGN PATENT DOCUMENTS

| | | |
|---|---|---|
| CN | 205542694 U | 8/2016 |
| CN | 205672359 U | 11/2016 |
| CN | 206118152 U | 4/2017 |
| CN | 206283706 U | 6/2017 |
| CN | 207743191 U | 8/2018 |
| RU | 96 487 U1 | 8/2010 |
| WO | 2020177775 A2 | 9/2020 |

* cited by examiner

X-RAY MACHINE HEAD AND IMAGE DEVICE

CROSS-REFERENCE TO RELATED APPLICATION

The present application is a continuation-in-part application of PCT Application No. PCT/CN2020/086352, filed Apr. 23, 2020, which claims priority to Chinese Application No. 201910166518.5, filed Mar. 6, 2019, both of which are incorporated herein by reference in their entirety.

FIELD OF THE INVENTION

The present invention relates to the field of X-ray instruments and devices, and in particular to an X-ray machine head and an image device.

DESCRIPTION OF THE PRIOR ART

The X-ray machines currently on the market are mainly divided into two types: X-ray machines equipped with combined X-ray machine heads, and gate-controlled X-ray machines.

As shown in FIG. 1, it is a combined X-ray machine head in the prior art. This device requires a high-voltage generating apparatus supporting an X-ray tube. The high-voltage generating apparatus is reduced in volume and is assembled with a tube core of the X-ray tube together into a sealed container filled with transformer oil to form an integrated X-ray generator. A filament transformer plays a role of isolation, an output filament AC voltage is several volts to tens of volts, and the current is from 0 A to 5.5 A. The combined X-ray machine head can be portable and used in conjunction with a mobile X-ray flat panel detector, or it can be mounted on a rack relative to a fixed ray acquisition apparatus such as an image intensifier or an X-ray flat panel detector to form a mobile X-ray machine, such as a typical C-arm or G-arm X-ray machine. This type of ray machine can be used for fluoroscopy and photographic inspection of various parts of a human body, or for surgery under image guidance.

As shown in FIG. 2, it is a gate-controlled X-ray machine in the prior art. FIG. 3 is a schematic diagram of the structure of a gate-controlled unit in the X-ray machine. The principle of the gate-controlled X-ray machine is to add a gate between a cathode filament and an anode target face of the X-ray tube, and control the occurrence and termination of X-rays by controlling the voltage of the gate. For ordinary X-ray machines, the working principle is to control the occurrence and termination of X-rays by loading and unloading the high voltage between the anode and the cathode. However, soft rays generated by an ordinary X-ray machine during the high voltage loading and unloading process will have an adverse effect, not only affecting the image quality, but also causing great harm to an examined human body. In contrast, the advantage of the gate-controlled X-ray machine is that it does not generate these soft rays, thus ensuring excellent imaging quality, and minimizing X-ray radiation damage to the examined human body.

On the basis of the gate-controlled technology, there has also been a technology that uses the principle of binocular stereo imaging to use a pair of rays with a certain angle to project an object under examination in turn and reconstruct a binocular stereo X-ray image.

Gate-controlled X-ray apparatuses have been applied to various large-scale and high-end X-ray machines to improve the quality of X-ray images, especially pulsed fluoroscopy images, while reducing the radiation damage to an examinee. But the gate-controlled X-ray machine also has obvious shortcomings. As shown in FIGS. 2 and 3, a gate-controlled voltage unit and the high-voltage generating apparatus are packaged together in a large-volume sealed and insulated oil tank filled with transformer oil. In addition, the gate-controlled voltage unit can also be individually packaged in a large-volume transformer oil tank. Normally, the high voltage generated by the high-voltage generating apparatus needs to be connected to the oil tank of the gate-controlled voltage unit through a high-voltage cable firstly, and then the gate-controlled voltage and the high voltage are connected to the X-ray tube through a multi-core high voltage cable together. As shown in FIG. 3, because a gate switch is directly controlled by a signal outside the transformer oil tank, an isolation transformer must be provided for the gate switch. In addition, a gate power supply also needs an isolation transformer.

In summary, in an existing gate-controlled X-ray apparatus, a total of at least four sets of isolation transformers are required, namely: high-voltage transformers, filament transformers, gate power supply transformers and gate switch transformers. This leads to a very complex structure and large volume of the entire system, with a typical volume exceeding 0.5 m*0.5 m*0.5 m. Because the oil tank containing the gate-controlled voltage unit is very complex and bulky, the gate-controlled technology has been unable to be used in combined X-ray machine heads which are mainly for mobile applications. In other words, all combined X-ray machine heads currently on the market are non-gate-controlled, which means that all current mobile X-ray device applications, especially surgical applications under C-arm X-ray fluoroscopy, cannot realize optimization of image qualities and reduction of radiation damages.

Therefore, there is a market demand for a device for X-ray imaging, which can be used in portable applications and can ensure a high imaging quality and a low radiation damage.

SUMMARY OF THE INVENTION

The purpose of the present invention is to provide an X-ray machine head and an image device, which solves problems of the complex structure and large volume of an existing gate-controlled X-ray apparatus, as well as the low imaging quality and large radiation damage of an existing combined X-ray machine head.

In order to solve the above technical problems, the present invention provides an X-ray machine head, which comprises:

a high-voltage DC power supply unit, a main module, and one or more X-ray tubes; wherein the high-voltage DC power supply unit generates a high-voltage DC voltage; and the negative pole of the high-voltage DC voltage is directly connected to the main module, and is also directly connected to a cathode filament of each of the one or more X-ray tubes;

wherein the main module is connected to a gate of each of the one or more X-ray tubes; and the main module is configured to provide a first voltage or a second voltage to the gate; and wherein the potential of the first voltage is equal to the potential of the negative pole of the high-voltage DC voltage, and the potential of the second voltage is lower than the potential of the negative pole of the high-voltage DC voltage.

Further, the main module comprises: a low-voltage DC power supply unit, one or more first switch units, one or more second switch units, and a central information processing unit;

wherein the low-voltage DC power supply unit is connected to the central information processing unit; the one or more first switch units are all connected to the central information processing unit; and the one or more second switch units are all connected to the central information processing unit;

wherein the low-voltage DC power supply unit generates multiple sets of low-voltage DC voltages; and the multiple sets of low-voltage DC voltages include: a first set of low-voltage DC voltages, a second set of low-voltage DC voltages and a third set of low-voltage DC voltages; wherein the negative pole of the first set of low-voltage DC voltages, the negative pole of the second set of low-voltage DC voltages, and the positive pole of the third set of low-voltage DC voltages are jointly connected to the negative pole of the high-voltage DC voltage; the positive pole of the third set of low-voltage DC voltages is also connected to an input end of each of the one or more first switch units; and the negative pole of the third set of low-voltage DC voltage is connected to an output end of each of the one or more second switch units;

wherein the positive pole and the negative pole of the second set of low-voltage DC voltages are both connected to the central information processing unit; and wherein the number of the first switch units is equal to the number of the second switch units, and is also equal to the number of gates of the X-ray tubes; and an output end of each of the one or more first switch units is correspondingly connected to an input end of each of the one or more second switch units, and the output end of each of the one or more first switch units is correspondingly connected to the gate of each of the X-ray tubes.

Further, the X-ray machine head further comprises: a housing, one or more filament power supply units, and a communication unit;

wherein the communication unit is connected to the central information processing unit;

wherein the high-voltage DC power supply unit, the low-voltage DC power supply unit, the one or more filament power supply units, the communication unit, the one or more first switch units, the one or more second switch units, the one or more X-ray tubes and the central information processing unit are all contained in the housing; and wherein the first set of low-voltage DC voltages are connected to each of the one or more filament power supply units.

Further, the housing is filled with an insulating medium, and the insulating medium circulates in the housing.

Further, the X-ray tubes comprise single-gate-controlled X-ray tubes, and the number of the single-gate-controlled X-ray tubes is equal to the number of the first switch units.

Further, two ends of an output voltage of each of the one or more filament power supply units are correspondingly connected to two ends of the cathode filament of each of the single-gate-controlled X-ray tubes.

Further, the positive pole of the high-voltage DC voltage is connected to the anode of each of the single-gate-controlled X-ray tubes, and the negative pole of the high-voltage DC voltage is connected to either end of the cathode filament of each of the single-gate-controlled X-ray tubes.

Further, the X-ray tubes comprise dual-gate-controlled X-ray tubes, and the number of the dual-gate-controlled X-ray tubes is equal to the half of the number of the first switch units.

Further, two ends of the output voltage of each of the one or more filament power supply units are correspondingly connected to two ends of each cathode filament of each of the dual-gate-controlled X-ray tubes.

Further, the positive pole of the high-voltage DC voltage is connected to the anode of each of the dual-gate-controlled X-ray tubes, and the negative pole of the high-voltage DC voltage is connected to either end of each cathode filament of each of the dual-gate-controlled X-ray tubes.

Further, each of the one or more filament power supply units has a signal input and feedback port, and all the signal input and feedback ports are connected to the central information processing unit.

Further, the communication unit is connected to an external power supply and control unit, and the external power supply and control unit is further connected to the low-voltage DC power supply unit and the high-voltage DC power supply unit.

Further, the communication unit is connected to the external power supply and control unit in a wired or wireless manner through a communication medium.

Further, a feedback signal end of the high-voltage DC power supply unit is connected to the external power supply and control unit.

Further, the central information processing unit comprises a single-chip microcomputer.

Further, the insulating medium comprises transformer oil.

Further, the volume of the housing is not more than 0.024 cubic meters.

The present invention provides an X-ray image device, which comprises an X-ray machine head, wherein the X-ray machine head comprises:

a high-voltage DC power supply unit, a main module, and one or more X-ray tubes; wherein the high-voltage DC power supply unit generates a high-voltage DC voltage; and the negative pole of the high-voltage DC voltage is directly connected to the main module, and is also directly connected to a cathode filament of each of the one or more X-ray tubes;

wherein the main module is connected to a gate of each of the one or more X-ray tubes; and the main module is configured to provide a first voltage or a second voltage to the gate; and wherein the potential of the first voltage is equal to the potential of the negative pole of the high-voltage DC voltage, and the potential of the second voltage is lower than the potential of the negative pole of the high-voltage DC voltage.

Further, the main module comprises: a low-voltage DC power supply unit, one or more first switch units, one or more second switch units, and a central information processing unit;

wherein the low-voltage DC power supply unit is connected to the central information processing unit; the one or more first switch units are all connected to the central information processing unit; and the one or more second switch units are all connected to the central information processing unit;

wherein the low-voltage DC power supply unit generates multiple sets of low-voltage DC voltages; and the multiple sets of low-voltage DC voltages include: a first set of low-voltage DC voltages, a second set of low-voltage DC voltages and a third set of low-voltage DC voltages; wherein the negative pole of the first set of low-voltage DC voltages, the negative pole of the second set of low-voltage DC voltages, and the positive pole of the third set of low-voltage DC voltages are jointly connected to the negative pole of the high-voltage DC voltage; the positive pole of the third set of low-voltage DC voltages is also connected to an input end of each of the one or more first switch units; and the negative pole of the third set of low-voltage DC voltage is connected to an output end of each of the one or more second switch units;

wherein the positive pole and the negative pole of the second set of low-voltage DC voltages are both connected to the central information processing unit; and wherein the number of the first switch units is equal to the number of the second switch units, and is also equal to the number of gates of the X-ray tubes; and an output end of each of the one or more first switch units is correspondingly connected to an input end of each of the one or more second switch units, and the output end of each of the one or more first switch units is correspondingly connected to the gate of each of the X-ray tubes.

Further, the X-ray machine head further comprises: a housing, one or more filament power supply units, and a communication unit;

wherein the high-voltage DC power supply unit, the low-voltage DC power supply unit, the one or more filament power supply units, the communication unit, the one or more first switch units, the one or more second switch units, the one or more X-ray tubes and the central information processing unit are all contained in the housing;

wherein the first set of low-voltage DC voltages are connected to each of the one or more filament power supply units; and wherein the housing is filled with an insulating medium, and the insulating medium circulates in the housing.

In a preferred embodiment of the present invention, the X-ray machine head comprises: a gate-controlled X-ray tube, a filament power supply unit, a first switch unit, a second switch unit, a high-voltage DC power supply unit, a low-voltage DC power supply unit, a central information processing unit and a communication unit that communicates with the outside. The basic working principle is as follows.

The high-voltage DC power supply unit is responsible for generating a high-voltage DC voltage in the range of 40 kV to 150 kV or more when a high voltage is loaded. The high-voltage DC voltage is loaded to the anode and cathode of the gate-controlled X-ray tube to accelerate electrons. Specifically, the positive pole of the high-voltage DC voltage is connected to the anode of the gate-controlled X-ray tube, and the negative pole of the high-voltage DC voltage is connected to either end of the cathode filament of the gate-controlled X-ray tube.

The low-voltage DC power supply unit provides three sets of low-voltage DC voltages to supply the filament power supply unit, the first switch unit, the second switch unit and the central information processing unit.

The filament power supply unit provides power to the filament in the gate-controlled X-ray tube to generate a filament current, thereby generating free electrons.

The first switch unit and the second switch unit can be used to select whether to provide a gate voltage to the gate in the X-ray tube.

The central information processing unit receives an external command through the communication unit to control the power supply to the gate by the first switch unit and the second switch unit. The central information processing unit also instructs the filament power supply unit to generate a filament current of a specified magnitude, and transmits an execution result to the outside of the X-ray machine head through the communication unit.

The specific working process is as follows:

The low-voltage DC power supply unit is controlled by the central information processing unit to generate three sets of low-voltage DC voltages, wherein the positive pole of one set of DC voltages is connected to the negative pole of the high-voltage DC voltage and is also connected to the input end of the first switch unit. The output end of the first switch unit is connected to the gate of the gate-controlled X-ray tube. When the central information processing unit obtains an external preliminary exposure command, the filament power supply unit is controlled to output a specified voltage to heat the cathode filament of the gate-controlled X-ray tube. At the same time, the high-voltage DC power supply unit has generated a high-voltage DC voltage under external control, the positive pole of the high-voltage DC voltage is loaded to the anode of gate-controlled X-ray tube, and the negative pole of the high-voltage DC voltage is loaded to the cathode filament of the gate-controlled X-ray tube. At this time, the first switch unit is turned off and the second switch unit is turned on, forming an electrical path between the gate and the negative pole of the third set of low-voltage DC voltages. The potential of the gate is equal to the potential of the negative pole the third set of low-voltage DC voltages, which is a lower potential than that of the negative pole of the high-voltage DC voltage. Since the filament is connected to the negative pole of the high-voltage DC voltage, the potential of the gate is lower than the potential of the filament. At this time, although the gate-controlled X-ray tube has been loaded with the high-voltage DC voltage generated by the high-voltage DC power supply unit, and the filament has been heated to a sufficient temperature, since the gate has a lower potential than that of the filament, electrons of the cathode filament are suppressed and cannot be emitted, so that X-rays cannot be generated.

When the central information processing unit receives an exposure instruction, under the control of the central information processing unit, the first switch unit is turned on and the second switch unit is turned off. At this time, an electrical path is formed between the gate and the negative pole of the high-voltage DC voltage. The potential of the gate is equal to the potential of the negative pole of the high-voltage DC voltage. Since the filament is also connected to the negative pole of the high-voltage DC voltage, the potential of the gate is equal to the potential of the filament. At this time, the electrons on the cathode filament can reach the anode of the X-ray tube under high-voltage acceleration, and X-rays are generated.

When it is desired to terminate the X-rays, the first switch unit is turned off and the second switch unit is turned on, forming an electrical path between the gate and the negative pole of the third set of low-voltage DC voltages. The potential of the gate is equal to the potential of the negative pole the third set of low-voltage DC voltages, which is a lower potential than that of the negative pole of the high-voltage DC voltage. Since the filament is connected to the negative pole of the high-voltage DC voltage, the potential of the gate is lower than the potential of the filament. Since the gate has a lower potential than that of the filament, the electrons of the cathode filament are suppressed and cannot be emitted, so that X-ray emission is terminated.

In order to provide a reasonable space for each of the above components in the smallest possible X-ray machine head and ensure their normal operation, considering that the working basic potentials of the filament and the gate are based on the cathode, the present invention has the following settings: two sets of negative poles and one set of positive poles of the three sets of low-voltage DC voltages output by the low-voltage DC power supply unit are all connected to the negative poles of the high-voltage DC power supply unit. This is an important beneficial technical means of the present invention. When the central information processing unit controls the filament power supply unit, the first switch unit and the second switch unit, when the filament power supply unit supplies power to the filament of the tube, when the first switch unit/the second switch unit supplies power to the gate of the tube, and when the central information processing unit exchanges information with the communication unit, it does not require any isolation transformer or take any other isolation measures, and the central information processing unit, the filament power supply unit, the first switch unit, the second switch unit, and the communication unit can all be arranged together compactly without worrying about mutual interference. Therefore, by using one isolation transformer in the low-voltage DC power supply unit, there is no need to use three isolation transformers, such as the filament transformer, the gate power transformer, and the gate switch transformer, as in the prior art. The X-ray machine head formed by all the components that are compactly arranged together will have a smaller volume, which is conducive to portable applications. Correspondingly, the communication between the communication unit and the outside of the X-ray machine head is in the form of optical fiber or wireless transmission.

The high-voltage DC power supply unit of the present invention can provide and maintain a high-voltage DC voltage at any specified time period, and apply it to the anode and cathode filaments of the gate-controlled X-ray tube, and by making the gate voltage of the X-ray tube equal to or lower than the potential of the cathode filament to control the occurrence and termination of X-rays, instead of controlling the emission and termination of X-rays by loading and unloading a high-voltage DC voltage as in traditional technical solutions. Therefore, this technical solution will not generate harmful soft rays caused by loading and unloading a high-voltage DC voltage, so that an excellent imaging quality can be obtained, and harmful X-ray radiation can also be reduced.

In some other embodiments, the purpose of the present invention is to solve the problem that a gate-controlled unit of a current X-ray machine is too complex and large to be integrated into a combined machine head which is already very crowded inside. A combined X-ray machine head is proposed, which not only realizes miniaturization of a gate-controlled system, but also frees up space inside an original combined machine head, and finally realizes a combined gate-controlled X-ray machine head, thereby improving the image quality and reducing the radiation damage.

The technical solution of another embodiment of the present invention is as follows: A combined X-ray machine head with a gate-controlled capability comprises a housing in which transformer oil is provided. A high-voltage DC power supply unit, a low-voltage DC power supply unit, a filament power supply unit, a communication unit, a high-speed and high-voltage electronic switch unit set, a gate-controlled X-ray tube and a central information processing unit are arranged in the transformer oil. An external power supply and control unit is also provided outside the housing. The high-voltage DC power supply unit is connected to the gate-controlled X-ray tube. The low-voltage DC power supply unit is connected to the filament power supply unit, the high-voltage electronic switch unit set, and the central information processing unit. The high-speed and high-voltage electronic switch unit set is connected to the gate-controlled X-ray tube and the central information processor unit. The filament power supply unit is connected to the gate-controlled X-ray tube and the central information processing unit. The communication unit is connected to the central information processing unit, and the communication unit is connected to the external power supply and control unit outside the housing in a wired or wireless manner. The transformer oil occupies the remaining space inside the housing, and the external power supply and control unit is connected to the central information processing unit, the high-voltage DC power supply unit, and the low-voltage DC power supply unit.

Further, the high-voltage DC power supply unit comprises a transformer, a rectifier diode, and a filter capacitor. The input end of the transformer of the high-voltage DC power supply unit is introduced from the outside of the housing. The output voltage of the transformer of the high-voltage DC power supply unit is rectified and stabilized by a corresponding rectifier diode and capacitor to generate a high-voltage DC voltage. The positive pole of the generated high-voltage DC voltage is connected to the anode of the gate-controlled X-ray tube, and the negative pole of the generated high-voltage DC voltage is connected to one end of the cathode filament of the gate-controlled X-ray tube; and a feedback signal end of the high-voltage DC power supply unit is connected to the external power supply and control unit.

Further, the low-voltage DC power supply unit comprises a transformer with multiple sets of output windings and corresponding rectifier diodes and filter capacitors. Voltages generated by the multiple sets of output windings of the transformer are rectified and stabilized by corresponding rectifier diodes and filter capacitors to generate multiple sets of low-voltage DC voltages. The first set of DC voltages of the multiple sets of low-voltage DC voltages are connected to the filament power supply unit, the second set of DC voltages of the multiple sets of low-voltage DC voltages are connected to the central information processing unit, and the negative poles of the first set of DC voltages and the second set of DC voltages are jointly connected to the negative pole of the high-voltage DC power supply unit and one end of the cathode filament of the gate-controlled X-ray tube. The third set of DC voltages of the multiple of sets of low-voltage DC voltages are connected to the high-speed and high-voltage electronic switch unit set and the negative pole of the high-voltage DC power supply unit.

Further, two ends of the output voltage of the filament power supply unit are correspondingly connected to two ends of the cathode filament of the gate-controlled X-ray tube, the filament power supply unit has a control input and feedback port, and the control input and the feedback port is connected to the central information processing unit.

Further, there are two sets of high-speed and high-voltage electronic switch units, namely a first high-speed and high-voltage electronic switch unit set and a second high-speed and high-voltage electronic switch unit set, and the gate-controlled X-ray tube is a dual-gate-controlled X-ray tube, or there are two gate-controlled X-ray tubes. There are two filament power supply units, and two ends of a power supply of each of the two filament power supply units are correspondingly connected to two ends of the two filaments in the dual-gate-controlled X-ray tube or two sets of gate-controlled X-ray tubes. The first high-speed and high-voltage electronic switch unit set comprises two first high-speed and high-voltage electronic switch units, and the second high-speed and high-voltage electronic switch unit set comprises two second high-speed and high-voltage electronic switch units. The first high-speed and high-voltage electronic switch unit and the second high-speed and high-voltage electronic switch unit each comprise one or more high-speed and high-voltage transistors and a control circuit. The output of the control circuit is connected to a control end of the high-speed and high-voltage transistors. An input signal end of the control circuit is connected to the central information processing unit. Input ends of the two first high-speed and high-voltage electronic switch units are connected to the positive pole of the third set of DC voltages. Output ends of the two first high-speed and high-voltage electronic switch units are correspondingly connected to input ends of the two corresponding second high-speed and high-voltage electronic switch units. At the same time, the output ends of the two first high-speed and high-voltage electronic switch units are respectively connected to corresponding gates of the dual-gate-controlled X-ray tube or the two gate-controlled X-ray tubes, and output ends of the two second high-speed and high-voltage electronic switch units are connected to the negative pole of the third set of DC voltages.

Further, there are two sets of high-speed and high-voltage electronic switch units, namely a first high-speed and high-voltage electronic switch unit set and a second high-speed and high-voltage electronic switch unit set. The first high-speed and high-voltage electronic switch unit set comprises one first high-speed and high-voltage electronic switch unit, and the second high-speed and high-voltage electronic switch unit set comprises one second high-speed and high-voltage electronic switch unit. The first high-speed and high-voltage electronic switch unit and the second high-speed and high-voltage electronic switch unit each comprise one or more high-speed and high-voltage transistors and a control circuit. The output of the control circuit is connected to a control end of the high-voltage and high-speed transistors. An input signal end of the control circuit is connected to the central information processing unit. The input end of the first high-speed and high-voltage electronic switch unit is connected to the positive pole of the third set of DC voltages, and the output end of the first high-speed and high-voltage electronic switch unit is connected to the input end of the corresponding second high-speed and high-voltage electronic switch unit and is also connected to a corresponding gate of the gate-controlled X-ray tube. The output end of the second high-speed and high-voltage electronic switch unit is connected to the negative pole of the third set of DC voltages.

Further, the gate-controlled X-ray tube is a dual-gate-controlled X-ray tube or two gate-controlled X-ray tubes. The positive pole of the high-voltage DC voltage generated by the high-voltage DC voltage unit is connected to the anodes of the dual-gate-controlled X-ray tube or the two gate-controlled X-ray tubes, and the negative pole of the high-voltage DC voltage generated by the high-voltage DC voltage unit is connected to each end of the two filament cathodes of the dual-gate-controlled X-ray tube or the two gate-controlled X-ray tubes.

Further, the communication unit comprises a wireless communication module A, and the wireless communication module A is connected to the central information processing unit. A wireless communication module B paired with the wireless communication module A is connected to the power supply and control unit outside the housing, and the central information processing unit realize parameter transferring and timing control with a power supply and control unit outside the housing by means of the wireless communication module A and the wireless communication module B.

Further, the volume of the housing is not more than 0.048 cubic meters.

Furthermore, the volume of the housing is not more than 0.024 cubic meters.

Through the design of the above functional components, an innovative gate-controlled and combined X-ray machine head can be realized.

In the technical solution of this embodiment, through the innovative system topology, comprising structural designs such as directly connecting a central information processing unit, which is highly susceptible to interference from electromagnetic field signals, to an internal high-voltage potential (up to 75 kv high-voltage pulse, hereinafter referred to as "high-voltage potential") which changes at a high speed, using an optical fiber module (or a wireless transmission module) to communicate with the outside, using a high-speed and high-voltage electronic switch module, and changing a gate-controlled circuit, a gate voltage feedback circuit, and a filament control circuit which are at low voltage potentials in a traditional gate-controlled X-ray apparatuses to work at high-voltage potentials and directly incorporating them into the central information processing unit, the number of high-voltage isolation transformers is reduced to a minimum, and at the same time, because they are all at high-voltage potentials, the central information processing unit, which has integrated the gate-controlled circuit, the gate voltage feedback circuit and the filament control circuit can be spatially integrated with the filament power supply unit, the high-speed and high-voltage electronic switch unit, the communication unit, etc., which not only realizes the miniaturization of the gate-controlled system, but also frees up a space inside the original combined machine head, so that the combined gate-controlled X-ray machine head is finally realized, thus improving the image quality and reducing the radiation damage.

The working process of the gate-controlled and combined machine head of this embodiment is that the central information processing unit obtains an external command and controls the filament power supply unit to output a specified voltage to heat the filament of the tube, and the high-voltage DC power supply unit generates a high voltage and sends it to the anode and the filament of the gate-controlled tube; at this time, the low-voltage power supply unit is also controlled by the central information processing unit to generate a gate-controlled voltage and send it to the gate of the tube through the high-speed and high-voltage electronic switch; under the control of a gate negative pressure, although the tube has been loaded with a high voltage and the filament has been heated to a sufficient temperature, the electrons of the filament cathode cannot be emitted and rays cannot be generated; and under the control of the central information processing unit, the high-speed and high-voltage electronic switch can be turned off and turned on to realize controlled exposure of X-rays. Since the gate has a certain capacitance, the gate still has residual charges when the voltage loaded on the gate is canceled, so a set of high-speed and high-voltage electronic switches need to be added to discharge the electrons in time to ensure that the gate voltage is completely zero volt and to ensure a reliable ray exposure.

The concept, specific structure and resulting technical effect of the present invention are further described below in conjunction with the drawings to fully understand the object, features, and effects of the present invention.

Figure 1:
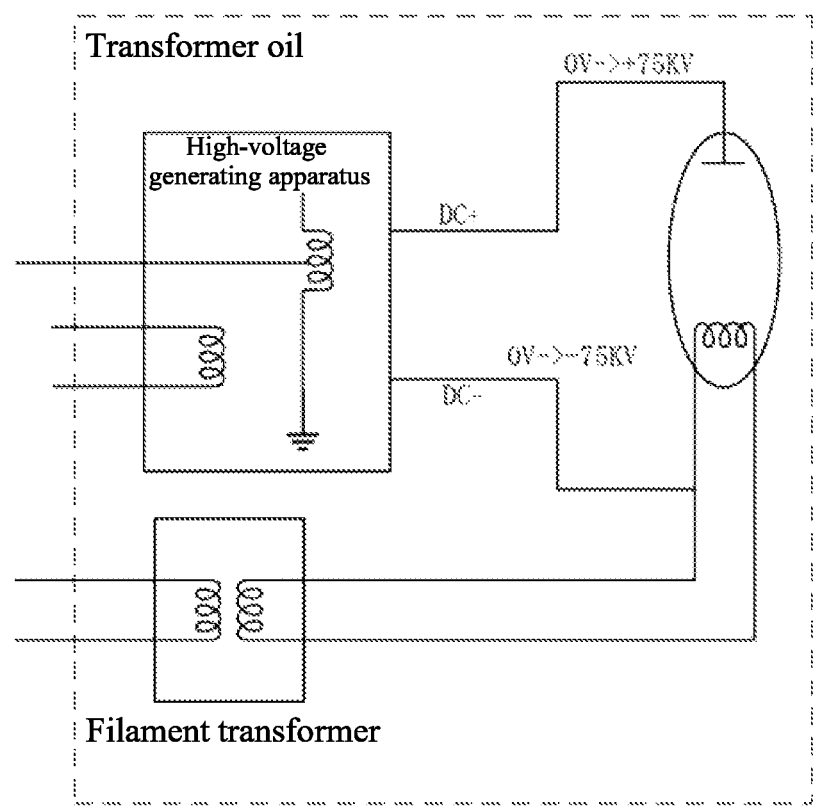
FIG. 1 is a schematic diagram of the structure of a combined X-ray machine head in the prior art.
Figure 2:
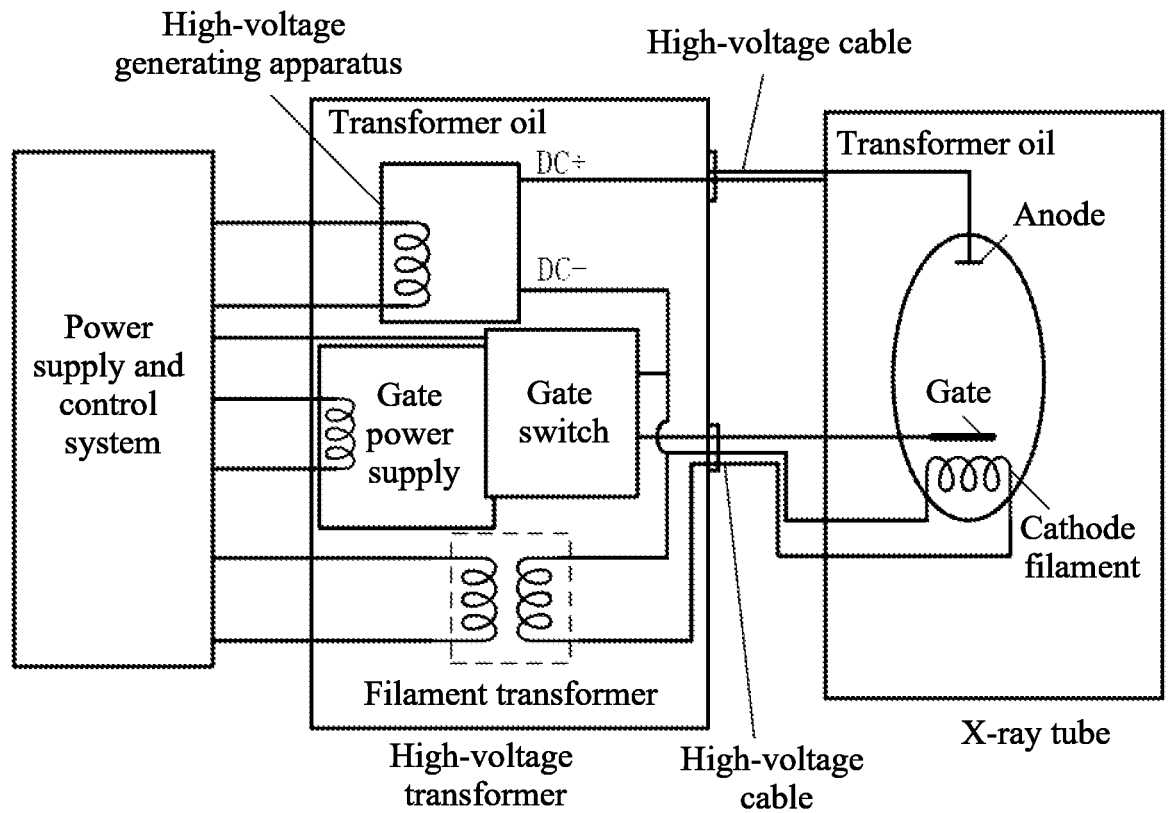
FIG. 2 is a schematic diagram of the structure of a gate-controlled X-ray machine in the prior art.
Figure 3:
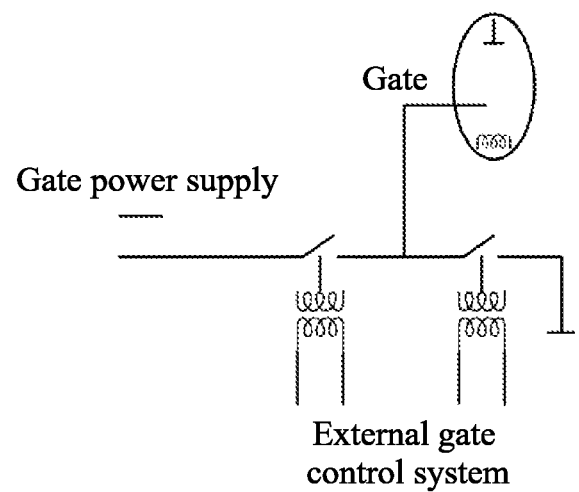
FIG. 3 is a schematic diagram of the structure of a gate-controlled unit in the prior art.

Components are labeled in the drawings as follows:

- 9 anode, 8 gate, 7 cathode filament;
- 100 housing, 101 transformer oil, 102 high-voltage DC power supply unit, 1021 feedback signal end, 103 low-voltage DC power supply unit, 104 filament power supply unit, 1041 control input and feedback output end, 105 communication unit, 106 first switch unit, 107 second switch unit, 108 gate-controlled X-ray tube, 109 central information processing unit, 110 communication medium, 111 external power supply and control unit, 112 main module;
- 200 housing, 201 transformer oil, 202 high-voltage DC power supply unit, 203 low-voltage DC power supply unit, 204 filament power supply unit, 205 communication unit, 206-1 first switch unit, 206-2 first switch unit, 207-1 second switch unit, 207-2 second switch unit, 208 gate-controlled X-ray tube, 209 central information processing unit, 210 communication medium; and
- 300 housing, 301 transformer oil, 302 high-voltage DC power supply unit, 303 low-voltage DC power supply unit, 304 filament power supply unit, 305 communication unit, 306-1 first switch unit, 306-2 first switch unit, 307-1 second Switch unit, 307-2 second switch unit, 308 gate-controlled X-ray tube, 309 central information processing unit, 310 communication medium.

DETAILED DESCRIPTION OF THE PREFERRED EMBODIMENTS

Preferred embodiments of the present invention are described below with reference to the drawings of the description to make the technical contents clearer and easier to understand. The present invention can be embodied in various forms of embodiments, and the scope of protection of the present invention is not limited to the embodiments mentioned herein.

In the drawings, the same numeral indicates components having the same structure, and similar numerals indicate assemblies having similar structures or functions throughout. The size and thickness of each assembly shown in the drawings are shown arbitrarily, and the size and thickness of each assembly are not limited in the present application. In order to make the illustration clearer, the thickness of the component in some places of the drawings is appropriately exaggerated.

Orientation terms mentioned in the present invention, such as "upper", "lower", "front", "rear", "left", "right", "inner", "outer", "side" etc., are merely orientations in the drawings and are only intended to explain and illustrate the present invention and are not intended to limit the scope of protection of the present invention.

When a certain assembly is described as "on" a further assembly, the assembly can be placed directly on the further assembly; and there may also be an intermediate assembly on which the assembly is placed, and the intermediate assembly is placed on the further assembly. When an assembly is described as "mounted to" or "connected to" a further assembly, it can be understood as either "mounted" or "connected" directly, or an assembly being indirectly "mounted to" or "connected to" the further assembly via an intermediate assembly.

Embodiment 1

Figure 4:
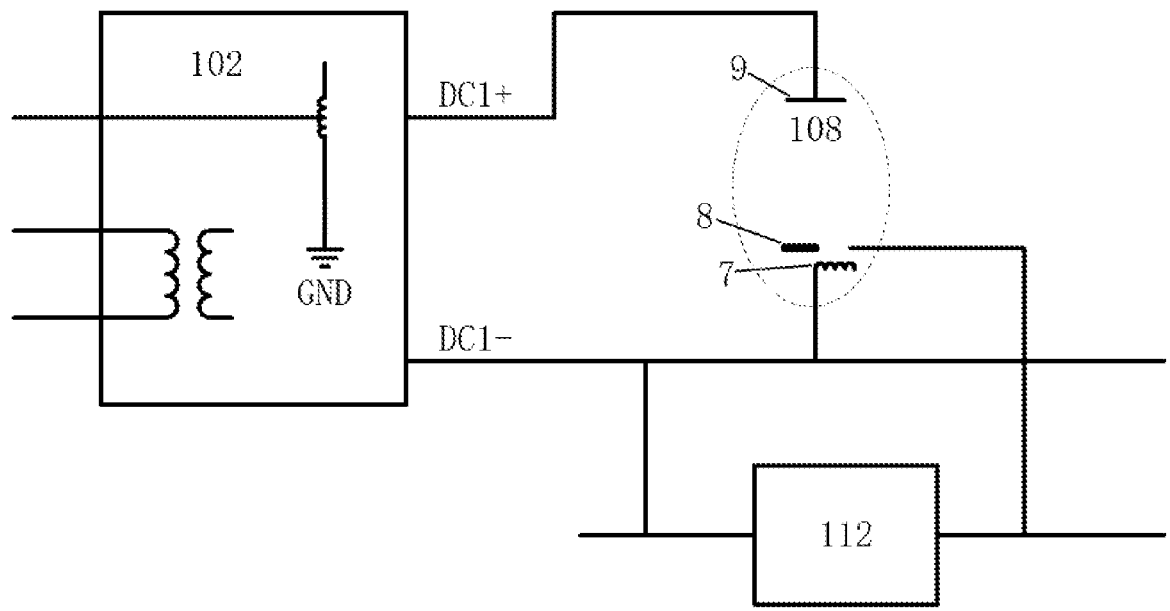
FIG. 4 is a schematic diagram of the constitution of an X-ray machine head containing a main module in Embodiment 1 of the present invention.

As shown in FIG. 4, this embodiment provides an X-ray machine head, comprising: a high-voltage DC power supply unit 102, a main module 112, and an X-ray tube 108. The high-voltage DC power supply unit 102 generates a high-voltage DC voltage; and the negative pole DC1− of the high-voltage DC voltage is directly connected to the main module 112, and DC1− is also directly connected to a cathode filament 7 of the X-ray tube 108. The main module 112 is connected to a gate 8 of the X-ray tube. The main module 112 can provide a first voltage or a second voltage to the gate 8. The potential of the first voltage is equal to the potential of the negative pole DC1− of the high-voltage DC voltage, and the potential of the second voltage is lower than the potential of the negative pole DC1− of the high-voltage DC voltage.

Figure 5:
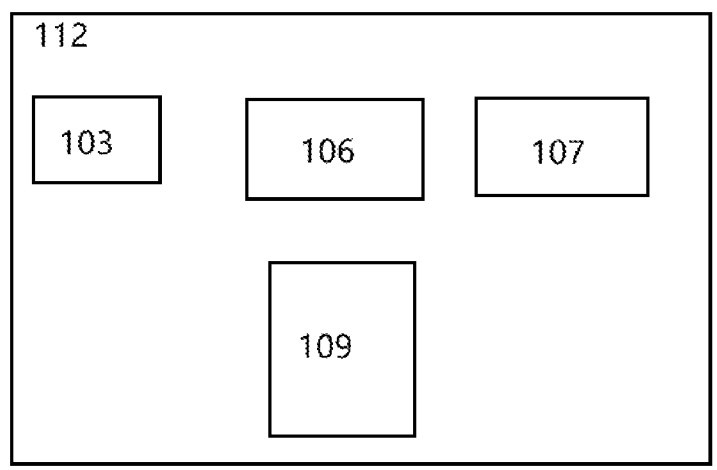
FIG. 5 is a schematic diagram of the constitution of a main module in Embodiment 1 of the present invention.

As shown in FIG. 5, the main module 112 comprises: a low-voltage DC power supply unit 103, a first switch unit 106, a second switch unit 107, and a central information processing unit 109.

Figure 6:
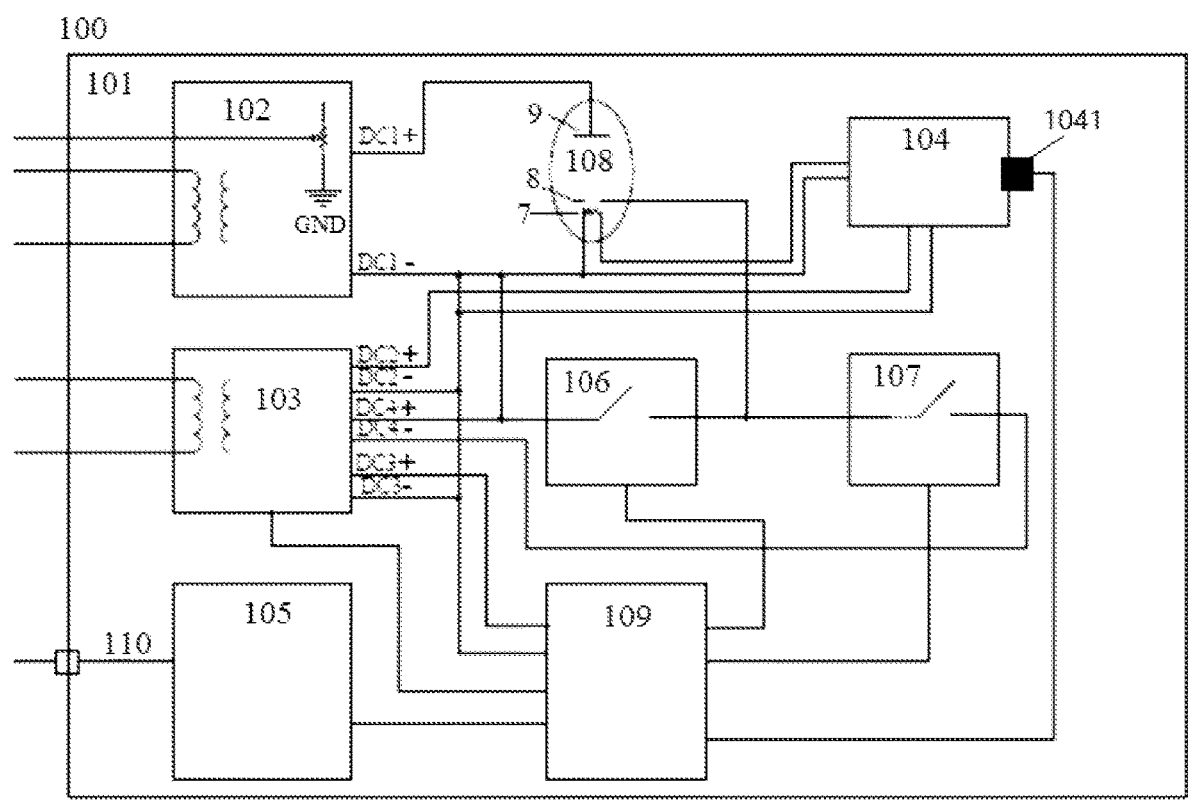
FIG. 6 is a schematic diagram of the structure of an X-ray machine head in Embodiment 1 of the present invention.
Figure 7:
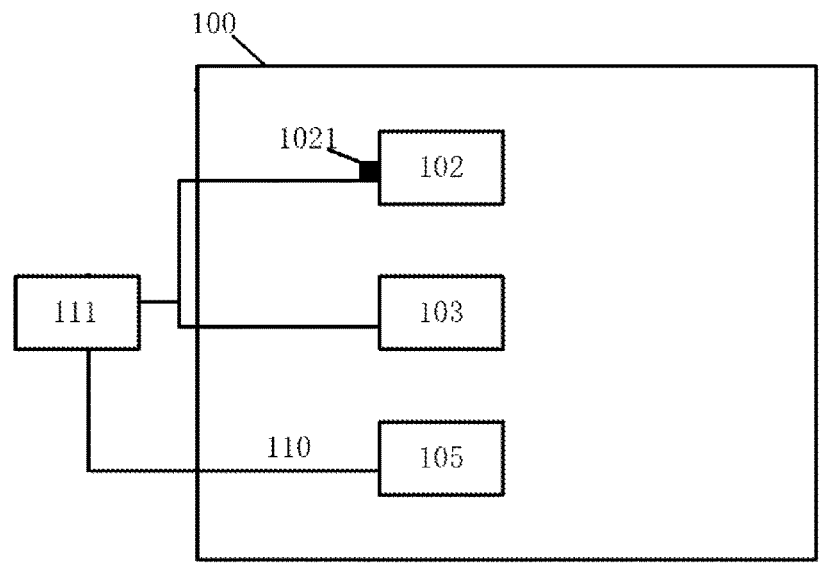
FIG. 7 is a schematic diagram of the connection between an external power supply and control unit and other components in Embodiment 1 of the present invention.

As shown in FIGS. 6 and 7, specifically, the X-ray machine head in this embodiment comprises: a housing 100, transformer oil 101, and the high-voltage DC power supply unit 102, the low-voltage DC power supply unit 103, a filament power supply unit 104, a communication unit 105, the first switch unit 106, the second switch unit 107, a gate-controlled X-ray tube 108 and the central information processing unit 109 which are immersed the in transformer oil 101. All components immersed in the transformer oil 101 are kept at a proper distance from the housing 100 to meet high-voltage insulation requirements. As shown in FIG. 7, an external power supply and control unit 111 is provided outside the housing 100, which is connected to the communication unit 105, the high-voltage DC power supply unit 102 and the low-voltage DC power supply unit 103.

A wire of a primary coil of a transformer of the high-voltage DC power supply unit 102 and a signal feedback output wire thereof, a wire of a primary coil of a transformer of the low-voltage DC power supply unit 103, and a communication medium 110 connected to the communication unit 105 are all led out of the housing 100. The communication medium 110 may be an optical fiber or a wireless communication medium.

The high-voltage DC power supply unit 102 comprises a transformer, a rectifier diode, and a filter capacitor. The primary coil and a secondary coil of the transformer of the high-voltage DC power supply unit 102 are insulated by an insulating paper or other high-insulating materials. The transformer of the high-voltage DC power supply unit 102 comprises a set of output coils, and a high-voltage DC voltage is obtained after rectifying and filtering by the rectifier diode and the filter capacitor, wherein the positive pole is DC1+ and the negative pole is DC1−. The transformer of the high-voltage DC power supply unit 102 may also comprise two sets of output coils, and two sets of AC voltages are rectified and filtered by the rectifier diode and the filter capacitor to generate, in series, a high-voltage DC voltage, wherein the positive pole is DC1+ and the negative pole is DC1−.

In this embodiment, the gate-controlled X-ray tube 108 is a single-gate-controlled X-ray tube. The positive pole DC1+ of the high-voltage DC voltage is connected to the anode 9 of the gate-controlled X-ray tube 108, and the negative pole DC1− is connected to either end of the cathode filament 7 of the gate-controlled X-ray tube 108. The rectification mode of the high-voltage DC power supply unit 102 is full-wave rectification or voltage doubler rectification. The high-voltage DC power supply unit 102 has a feedback signal end 1021, and the feedback signal end 1021 outputs a high-voltage voltage feedback signal to the external power supply and control unit 111.

The low-voltage DC power supply unit 103 comprises a transformer with three sets of output windings and corresponding rectifier diodes and filter capacitors. The primary coil and a secondary coil of the transformer of the low-voltage DC power supply unit 103 are insulated by an insulating paper or other high-insulating materials. After AC voltages generated by three output coils corresponding to the three sets of output windings of the transformer are rectified and filtered, three sets of low-voltage DC voltages are generated respectively as internal working voltages. The positive pole of the first set of low-voltage DC voltages is DC2+, and the negative pole is DC2−; the positive pole of the second set of low-voltage DC voltages is DC3+, and the negative pole is DC3−; and the positive pole of the third set of low-voltage DC voltages is DC4+, and the negative pole is DC4−.

For the low-voltage DC power supply unit 103, a voltage control chip is used to generate the above three sets of low-voltage DC voltages with controlled voltages. A voltage control end of the low-voltage DC power supply unit 103 is connected to the central information processing unit 109, and voltage activation of the low-voltage DC power supply unit 103 is controlled by the central information processing unit 109 to realize pulse control over DC2+/DC2−, DC3+/DC3−, and DC4+/DC4− and to save energy when the system is sleeping.

The positive pole DC3+ and the negative pole DC3− of the second set of low-voltage DC voltages are both connected to the central information processing unit 109, the positive pole DC2+ and the negative pole DC2− of the first set of low-voltage DC voltages are both connected to the filament power supply unit 104, and DC2− and DC3− are also jointly connected to the DC1− terminal of the high-voltage DC power supply unit 102.

The filament power supply unit 104 outputs a pulse-width modulated low voltage, two ends of a power output of the filament power supply unit 104 are connected to two ends of the cathode filament 7 of the gate-controlled X-ray tube 108, and a control input and feedback output end 1041 of the filament power supply unit 104 is connected to the central information processing unit 109.

In this embodiment, when an optical fiber is used as the communication medium 110, the communication unit 105 comprises a high-speed communication element that mutually converts optical signals and electrical signals. An optical signal interface terminal of the high-speed communication element is connected to the optical fiber, and an electrical signal terminal of the high-speed communication element is connected to the central information processing unit 109. The other end of the optical fiber is connected to an optical fiber terminal fixed on the housing 100, and the function of the communication unit 105 is to exchange commands and parameters between the central information processing unit 109 and the external power supply and control unit.

Both the first switch unit 106 and the second switch unit 107 comprise one or more high-speed and high-voltage transistors and a control circuit (such as an optocoupler transformer), wherein an output end of the control circuit is connected to a control end of the high-speed and high-voltage transistor, and a control signal of the control circuit is connected to the central information processing unit 109. An input end of the first switch unit 106 is connected to DC1− of the high-voltage DC power supply unit 102 and DC4+, an output end of the first switch unit 106 is connected to the gate 8 of the gate-controlled X-ray tube 108 and is also connected to an input end of the second switch unit 107, and an output end of the second switch unit 107 is connected to DC4−.

The central information processing unit 109 can be a single-chip microcomputer, an ARM processor or a DSP chip, which is responsible for executing external instructions, including exposure and termination, X-ray tube current and exposure timing, etc., and feeding back internal working status and parameters of the X-ray machine head to the outside. The central information processing unit 109 realizes control of exposure/termination and exposure timing by controlling the on/off of the first switch unit 106/the second switch unit 107. The central information processing unit 109 also realizes current control of the gate-controlled X-ray tube by controlling the filament power supply unit 104.

The working principle and process of this embodiment are as follows.

The low-voltage DC power supply unit 103 is controlled by the central information processing unit 109 to generate three sets of low-voltage DC voltages. The positive pole of the first set of low-voltage DC voltages is DC2+, and the negative pole is DC2−; the positive pole of the second set of low-voltage DC voltages is DC3+, and the negative pole is DC3−; and the positive pole of the third set of low-voltage DC voltages is DC4+, and the negative pole is DC4−. When the central information processing unit 109 obtains an external preliminary exposure command, the filament power supply unit 104 is controlled to output a specified voltage to heat the cathode filament 7 of the gate-controlled X-ray tube 108. At the same time, the high-voltage DC power supply unit 102 has generated a high-voltage DC voltage under external control, the positive pole DC1+ of the high-voltage DC voltage is applied to the anode 9 of the gate-controlled X-ray tube, and at the same time, the negative pole DC1− of the high-voltage DC voltage is loaded to the cathode filament 7 of the gate-controlled X-ray tube. At this time, the first switch unit 106 is turned off and the second switch unit 107 is turned on, forming an electrical path between the gate 8 and the negative pole DC4− of the third set of low-voltage DC voltages. The potential of the gate 8 is equal to the potential of the negative pole DC4− of the third set of low-voltage DC voltages, which is a lower potential than that of the negative pole DC1− of the high-voltage DC voltage. That is, the second voltage provided by the first module 112 to the gate 8 is lower than the voltage of DC1−. Since the cathode filament is connected to the negative pole DC1− of the high-voltage DC voltage, the potential of the gate 8 is lower than the potential of the cathode filament 7. At this time, although the gate-controlled X-ray tube 108 has been loaded with the high-voltage DC voltage generated by the high-voltage DC power supply unit, and the filament 7 has been heated to a sufficient temperature, since the gate 8 has a lower potential than that of the filament 7, electrons of the cathode filament 7 are suppressed and cannot be emitted, so that X-rays cannot be generated.

When the central information processing unit 109 receives an exposure instruction, under the control of the central information processing unit 109, the first switch unit 106 is turned on and the second switch unit 107 is turned off. At this time, an electrical path is formed between the gate 8 and the negative pole DC1− of the high-voltage DC voltage. The first voltage provided by the first module 112 to the gate 8 is equal to that of DC1−. The potential of the gate 8 is equal to the potential of the negative pole DC1− of the high-voltage DC voltage. Since the cathode filament 7 is also connected to the negative pole DC1− of the high-voltage DC voltage, the potential of the gate 8 is equal to the potential of the cathode filament 7. At this time, the electrons on the cathode filament 7 can reach the anode 9 of the X-ray tube 108 under high-voltage acceleration, and X-rays are generated.

When it is desired to terminate the X-rays, the first switch unit 106 is turned off and the second switch unit 107 is turned on, forming an electrical path between the gate 8 and the negative pole DC4− of the third set of low-voltage DC voltages. The potential of the gate 8 is equal to the potential of the negative pole DC4− of the third set of low-voltage DC voltages, which is a lower potential than that of the negative pole DC1− of the high-voltage DC voltage. That is, the second voltage provided by the first module 112 to the gate 8 is lower than the voltage of DC1−. Since the cathode filament is connected to the negative pole DC1− of the high-voltage DC voltage, the potential of the gate 8 is lower than the potential of the cathode filament 7, so that the electrons of the cathode filament 7 are suppressed and X-ray emission is terminated.

Embodiment 2

Figure 8:
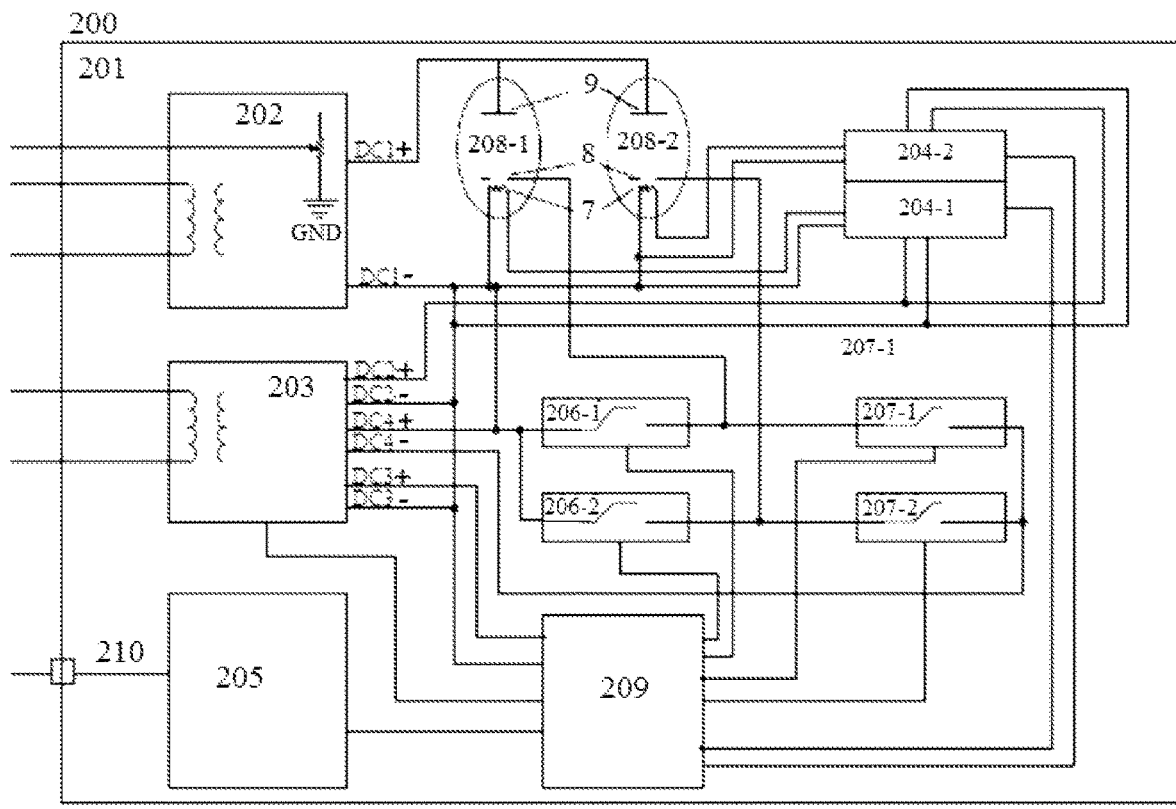
FIG. 8 is a schematic diagram of the structure of an X-ray machine head in Embodiment 2 of the present invention.

As shown in FIG. 8, this embodiment provides an X-ray machine head, comprising a housing 200, and transformer oil 201, a high-voltage DC power supply unit 202, a low-voltage DC power supply unit 203, two filament power supply units 204-1 and 204-2, a communication unit 205, a set of two first switch units 206-1 and 206-2, a set of two second switch units 207-1 and 207-2, two gate-controlled X-ray tubes 208-1 and 208-2, and a central information processing unit 209 that are provided in the housing 200. An external power supply and control unit (not shown in FIG. 8) is provided outside the housing 200. Except that a wire of a primary coil of a transformer of the high-voltage DC power supply unit 202 and a signal output feedback wire thereof, a wire of a primary coil of a transformer of the low-voltage DC power supply unit 203, and a communication medium 210 connected to the communication unit 205 need to be led out of the housing 200, the rest parts are all immersed in transformer oil 201 and kept a sufficient distance from the housing 200 to meet the high-voltage insulation requirements.

The high-voltage DC power supply unit 202 comprises a transformer, a rectifier diode, and a filter capacitor. The primary coil and a secondary coil of the transformer of the high-voltage DC power supply unit 202 are insulated by an insulating paper or other high-insulating materials. The transformer of the high-voltage DC power supply unit 202 comprises a set of output coils, and a high-voltage DC voltage is obtained after rectifying and filtering by the rectifier diode and the filter capacitor. The positive pole of the high-voltage DC voltage is DC1+, and the negative pole is DC1−. The transformer of the high-voltage DC power supply unit 202 may also comprise two sets of output coils, and two sets of AC voltages are rectified and filtered by the rectifier diode and the filter capacitor to generate, in series, a high-voltage DC voltage. The positive pole of the high-voltage DC voltage is DC1+, and the negative pole is DC1−. The gate-controlled X-ray tubes 208-1 and 208-2 are two single-gate-controlled X-ray tubes. DC1+ is connected to the anode 9 of each of the two single-gate-controlled X-ray tubes, and DC1− is connected to either end of the cathode filament 7 of each of the two single-gate-controlled X-ray tubes. The rectification mode of the high-voltage DC power supply unit 202 is full-wave rectification or voltage doubler rectification. The high-voltage DC power supply unit 202 has a voltage/current feedback signal output terminal, and the signal output terminal is connected to the external power supply and control unit.

The low-voltage DC power supply unit 203 comprises a transformer with three sets of output windings and corresponding rectifier diodes and filter capacitors. The primary coil and a secondary coil of the transformer of the low-voltage DC power supply unit 203 are insulated by an insulating paper or other high-insulating materials. After AC voltages generated by the three output coils of the three sets of output windings are rectified and filtered by the rectifier diodes and the filter capacitors, three sets of low-voltage DC voltages are generated as internal working voltages. The positive pole of the first set of low-voltage DC voltages is DC2+, and the negative pole is DC2−; the positive pole of the second set of low-voltage DC voltages is DC3+, and the negative pole is DC3−; and the positive pole of the third set of low-voltage DC voltages is DC4+, and the negative pole is DC4−.

For the low-voltage DC power supply unit 203, a voltage control chip is used to generate three sets of low-voltage DC voltages DC2+/DC2−, DC3+/DC3−, and DC4+/DC4− with controlled voltages. A voltage control end of the low-voltage DC power supply unit 203 is connected to the central information processing unit 209, and voltage activation of the low-voltage DC power supply unit 203 is controlled by the central information processing unit 209 to realize pulse control over DC2+/DC2−, DC3+/DC3−, and DC4+/DC4− and to save energy when the system is sleeping.

As shown in FIG. 8, the positive pole DC3+ and the negative pole DC3− of the second set of low-voltage DC voltages are both connected to the central information processing unit 209, the positive pole DC2+ and the negative pole DC2− of the first set of low-voltage DC voltages are both connected to two filament power supply units 204-1 and 204-2, and DC2− and DC3− are also jointly connected to the negative pole DC1− of the high-voltage DC voltage output by the high-voltage DC power supply unit 202.

The output of one filament power supply unit 204-1 is a pulse-width modulated low voltage. Two ends of a power supply of the filament power supply unit 204-1 are connected to two ends of the cathode filament 7 of the gate-controlled X-ray tube 208-1. A control input and feedback output end of the filament power supply unit 204-1 is connected to the central information processing unit 209.

The output of the other filament power supply unit 204-2 is a pulse-width modulated low voltage. Two ends of a power supply of the filament power supply unit 204-2 are connected to two ends of the filament of the gate-controlled X-ray tube 208-2. A control input and feedback output end of the filament power supply unit 204-2 is connected to the central information processing unit 209.

In this embodiment, when an optical fiber is used as the communication medium 210, the communication unit 205 comprises a high-speed communication element that mutually converts optical signals and electrical signals. An optical signal interface terminal of the high-speed communication element is connected to the optical fiber, and an electrical signal terminal of the high-speed communication element is connected to the central information processing unit 209. The other end of the optical fiber is connected to an optical fiber terminal fixed on the housing 200, and the function of the communication unit 205 is to exchange commands and parameters between the central information processing unit 209 and the external power supply and control unit.

In this embodiment, a total of four switch units are used, which are two first switch units 206-1 and 206-2, and two second switch units 207-1 and 207-2, respectively. Each of these four switch units comprises one or more high-speed and high-voltage transistors and a control circuit (such as an optocoupler transformer). An output end of the control circuit is connected to a control end of the high-speed and high-voltage transistor, and a control signal of the control circuit is connected to the central information processing unit 209. Input ends of the two first switch units 206-1 and 206-2 are both connected to DC1− of the high-voltage DC power supply unit 202 and DC4+. An output end of the first switch unit 206-1 is connected to a gate 8 of the gate-controlled X-ray tube 208-1, and is also connected to an input end of the second switch unit 207-1. An output end of the second switch unit 207-1 is connected to DC4−, and an output end of the first switch unit 206-2 is connected to a gate 8 of the gate-controlled X-ray tube 208-2 and is also connected to an input end of the second switch unit 207-2. An output end of the second switch unit 207-2 is connected to DC4−.

The central information processing unit 209 can be a single-chip microcomputer, an ARM processor or a DSP chip, which is responsible for executing external instructions, including exposure and termination, X-ray tube current and exposure timing, etc., and feeding back internal working status and parameters of the X-ray machine head to the outside. The central information processing unit 209 realizes control of exposure/termination and exposure timing by controlling the on/off of the four switch units. The central information processing unit 209 also realizes current control of the gate-controlled X-ray tube 208-1 by controlling the filament power supply unit 204-1, and realizes current control of the gate-controlled X-ray tube 208-2 by controlling the filament power supply unit 204-2.

The working principle and process of this embodiment are as follows.

The low-voltage DC power supply unit 203 is controlled by the central information processing unit 209 to generate three sets of low-voltage DC voltages. The positive pole of the first set of low-voltage DC voltages is DC2+, and the negative pole is DC2−; the positive pole of the second set of low-voltage DC voltages is DC3+, and the negative pole is DC3−; and the positive pole of the third set of low-voltage DC voltages is DC4+, and the negative pole is DC4−. When the central information processing unit 209 obtains an external preliminary exposure command, the filament power supply unit 204-1 is controlled to output a specified voltage to heat the cathode filament 7 of the gate-controlled X-ray tube 208-1. At the same time, the high-voltage DC power supply unit 202 has generated a high-voltage DC voltage under external control, the positive pole DC1+ of the high-voltage DC voltage is applied to the anode 9 of the gate-controlled X-ray tube, and at the same time, the negative pole DC1− of the high-voltage DC voltage is loaded to the cathode filament 7 of the gate-controlled X-ray tube. At this time, the first switch unit 206-1 is turned off and the second switch unit 207-1 is turned on, forming an electrical path between the gate 8 and the negative pole DC4− of the third set of low-voltage DC voltages. The potential of the gate 8 is equal to the potential of the negative pole DC4− of the third set of low-voltage DC voltages, which is a lower potential than that of the negative pole DC1− of the high-voltage DC voltage. Since the cathode filament 7 is connected to the negative pole DC1− of the high-voltage DC voltage, the potential of the gate 8 is lower than the potential of the cathode filament 7. At this time, although the gate-controlled X-ray tube 208-1 has been loaded with the high-voltage DC voltage generated by the high-voltage DC power supply unit, and the cathode filament 7 has been heated to a sufficient temperature, since the gate 8 has a lower potential than that of the filament 7, electrons of the cathode filament 7 are suppressed and cannot be emitted, so that X-rays cannot be generated.

When the central information processing unit 209 receives an exposure instruction, under the control of the central information processing unit 209, the first switch unit 206-1 is turned on and the second switch unit 207-1 is turned off. At this time, an electrical path is formed between the gate 8 and the negative pole DC1− of the high-voltage DC voltage. The potential of the gate 8 is equal to the potential of the negative pole DC1− of the high-voltage DC voltage. Since the cathode filament 7 is also connected to the negative pole DC1− of the high-voltage DC voltage, the potential of the gate 8 is equal to the potential of the cathode filament 7. At this time, the electrons on the cathode filament 7 can reach the anode 9 of the X-ray tube 208-1 under high-voltage acceleration, and X-rays are generated.

When it is desired to terminate the X-rays, the first switch unit 206-1 is turned off and the second switch unit 207-1 is turned on, forming an electrical path between the gate 8 and the negative pole DC4− of the third set of low-voltage DC voltages. The potential of the gate 8 is equal to the potential of the negative pole DC4− of the third set of low-voltage DC voltages, which is a lower potential than that of the negative pole DC1− of the high-voltage DC voltage. Since the cathode filament 7 is connected to the negative pole DC1− of the high-voltage DC voltage, the potential of the gate 8 is lower than the potential of the cathode filament 7, so that the electrons of the cathode filament 7 are suppressed and X-ray emission is terminated.

It should be noted that, for ease of description, the situation described in this embodiment is that two first switch units and two second switch units are used to control respective gates of the two gate-controlled X-ray tubes. It is easy to understand and realize that, based on the same principle, when the gate-controlled X-ray tube is a single-gate-controlled X-ray tube, N first switch units and N second switch units can be used to control respective gates of N gate-controlled X-ray tubes.

Embodiment 3

Figure 9:
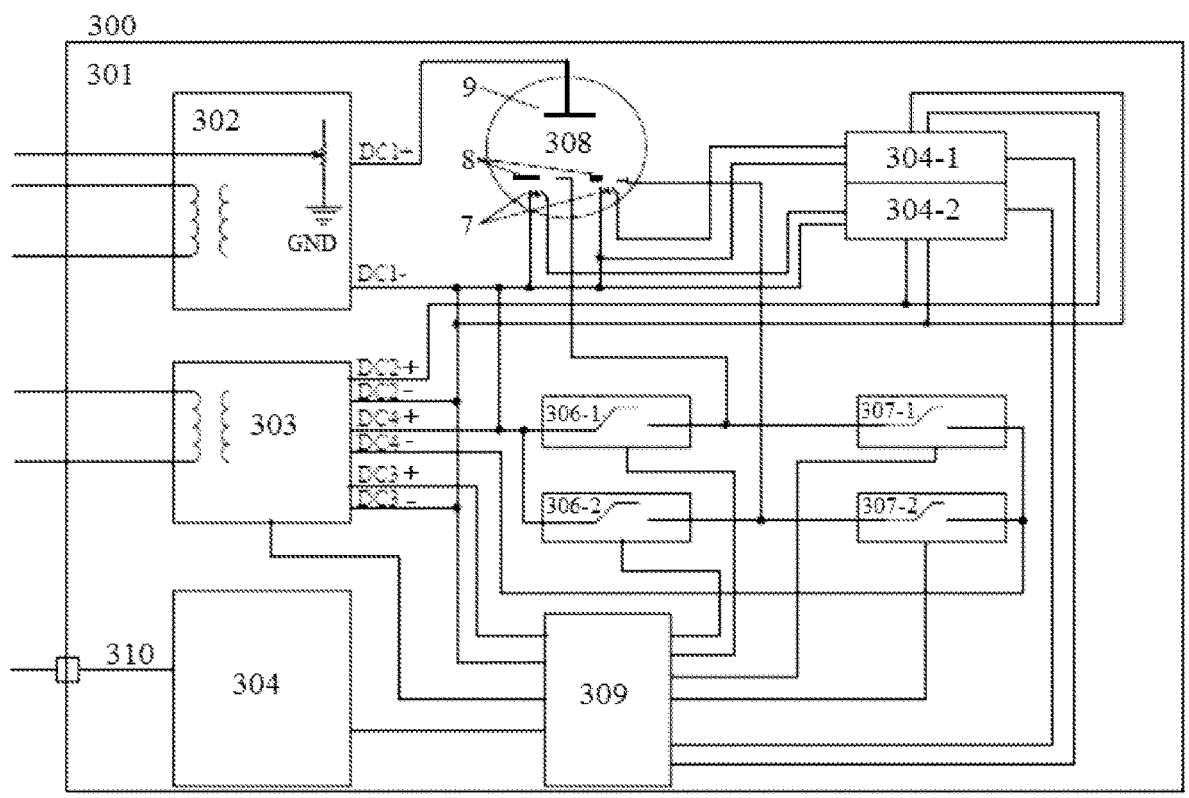
FIG. 9 is a schematic diagram of the structure of an X-ray machine head in Embodiment 3 of the present invention.

As shown in FIG. 9, this embodiment provides an X-ray machine head, comprising a housing 300, transformer oil 301 contained in the housing 300, and a high-voltage DC power supply unit 302, a low-voltage DC power supply unit 303, two filament power supply units 304-1 and 304-2, a communication unit 305, two first switch units 306-1 and 306-2, two second switch units 307-1 and 307-2, a dual-gate-controlled X-ray tube 308 and a central information processing unit 309 that are immersed in the transformer oil 301. An external power supply and control unit (not shown in FIG. 9) is also provided outside the housing 300. A wire of a primary coil of a transformer of the high-voltage DC power supply unit 302 and a signal output feedback wire thereof, a wire of a primary coil of a transformer of the low-voltage DC power supply unit 303, and a communication medium 310 connected to the communication unit 305 are all led out of the housing 300. The rest components are all immersed in the transformer oil 301 and kept a sufficient distance from the housing 300 to meet high-voltage insulation requirements.

The high-voltage DC power supply unit 302 comprises a transformer, a rectifier diode, and a filter capacitor. The primary coil and a secondary coil of the transformer are insulated by an insulating paper or other high-insulating materials. The transformer of the high-voltage DC power supply unit 302 may comprise a set of output coils, and a high-voltage DC voltage is obtained after rectifying and filtering by the rectifier diode and the filter capacitor. The high voltage terminal of the high-voltage DC voltage is DC1+, and the low voltage terminal is DC1−. The transformer of the high-voltage DC power supply unit 302 may also comprise two sets of output coils, and two sets of AC voltages are rectified and filtered by the rectifier diode and the filter capacitor to generate, in series, a high-voltage DC voltage. The positive pole of the high-voltage DC voltage is DC1+, and the negative pole is DC1−.

The gate-controlled X-ray tube 308 is a dual-gate-controlled X-ray tube, which has an anode 9, two gates 8 and two cathode filaments 7.

DC1+ is connected to the anode 9 of the gate-controlled X-ray tube 308, and DC1− is connected to respective ends of the two cathode filaments 7 of the gate-controlled X-ray tube 308. The rectification mode of the high-voltage DC power supply unit 302 is full-wave rectification or voltage doubler rectification. The high-voltage DC power supply unit 302 has a voltage/current feedback signal output terminal, and the signal output terminal is connected to the external power supply and control unit.

The low-voltage DC power supply unit 303 comprises a transformer with three sets of output windings and corresponding rectifier diodes and filter capacitors. The primary coil and a secondary coil of the transformer of the low-voltage DC power supply unit 303 are insulated by an insulating paper or other high-insulating materials. After AC voltages generated by the three output coils of the three output windings are rectified and filtered, three sets of low-voltage DC voltages are generated as internal working voltages. The positive pole of the first set of low-voltage DC voltages is DC2+, and the negative pole is DC2−; the positive pole of the second set of low-voltage DC voltages is DC3+, and the negative pole is DC3−; and the positive pole of the third set of low-voltage DC voltages is DC4+, and the negative pole is DC4−.

For the low-voltage DC power supply unit 303, a voltage control chip is used to generate three sets of low-voltage DC voltages with controlled voltages. A voltage control end of the low-voltage DC power supply unit 303 is connected to the central information processing unit 309. Voltage activation of the low-voltage DC power supply unit 303 is controlled by the central information processing unit 309 to realize pulse control over the three sets of low-voltage DC voltages DC2+/DC2−, DC3+/DC3−, and DC4+/DC4− and to save energy when the system is sleeping.

As shown in FIG. 9, the positive pole DC3+ and the negative pole DC3− of the second set of low-voltage DC voltages are both connected to the central information processing unit 309, the positive pole DC2+ and the negative pole DC2− of the first set of low-voltage DC voltages are both connected to two filament power supply units 304-1 and 304-2, and DC2− and DC3− are also jointly connected to the negative pole DC1− of the high-voltage DC voltage output by the high-voltage DC power supply unit 302.

The output of the filament power supply unit 304-1 is a pulse-width modulated low voltage. Two ends of a power output of the filament power supply unit 304-1 are connected to two ends of one cathode filament 7 of the gate-controlled X-ray tube 308, and a control input and feedback output end of the filament power supply unit 304-1 is connected to the central information processing unit 309.

The filament power supply unit 304-2 outputs a pulse-width modulated low voltage, two ends of a power of the filament power supply unit 304-2 are connected to two ends of the other cathode filament 7 of the gate-controlled X-ray tube 308, and a control input and feedback output end of the filament power supply unit 304-2 is connected to the central information processing unit 309.

In this embodiment, when an optical fiber is used as the communication medium 310, the communication unit 305 comprises a high-speed communication element that mutually converts optical signals and electrical signals. An optical signal interface terminal of the high-speed communication element is connected to the optical fiber, and an electrical signal terminal of the high-speed communication element is connected to the central information processing unit 309. The other end of the optical fiber is connected to an optical fiber terminal fixed on the housing 300, and the function of the communication unit 305 is to exchange commands and parameters between the central information processing unit 309 and the external power supply and control unit.

In this embodiment, a total of four switch units are used, which are two first switch units 306-1 and 306-2, and two second switch units 307-1 and 307-2, respectively. Each of these four switch units comprises one or more high-speed and high-voltage transistors and a control circuit (such as an optocoupler transformer). An output end of the control circuit is connected to a control end of the high-speed and high-voltage transistor, and a control signal of the control circuit is connected to the central information processing unit 309. Input ends of the two first switch units 306-1 and 306-2 are both connected to DC1− of the high-voltage DC power supply unit 302 and DC4+. An output end of the first switch unit 306-1 is connected to one gate 8 of the gate-controlled X-ray tube 308, and is also connected to an input end of the second switch unit 307-1. An output end of the second switch unit 307-1 is connected to DC4−. An output end of the first switch unit 306-2 is connected to the other gate 8 of the gate-controlled X-ray tube 308, and is also connected to an input end of the second switch unit 307-2. An output end of the second switch unit 307-2 is connected to DC4−.

The central information processing unit 309 can be a single-chip microcomputer, an ARM processor or a DSP chip, which is responsible for executing external instructions, including exposure and termination, X-ray tube current and exposure timing, etc., and feeding back internal working status and parameters of the X-ray machine head to the outside. The central information processing unit 309 realizes control of exposure/termination and exposure timing by controlling the on/off of the four switch units. The central information processing unit 309 also realizes current control of the two cathode filaments 7 of the gate-controlled X-ray tube 308 by controlling the two filament power supply units 304-1 and 304-2.

The working principle and process of this embodiment are as follows.

The low-voltage DC power supply unit 303 is controlled by the central information processing unit 309 to generate three sets of low-voltage DC voltages. The positive pole of the first set of low-voltage DC voltages is DC2+, and the negative pole is DC2−; the positive pole of the second set of low-voltage DC voltages is DC3+, and the negative pole is DC3−; and the positive pole of the third set of low-voltage DC voltages is DC4+, and the negative pole is DC4−. When the central information processing unit 309 obtains an external preliminary exposure command, the filament power supply unit 304-1 is controlled to output a specified voltage to heat the cathode filament 7 of the gate-controlled X-ray tube 308. At the same time, the high-voltage DC power supply unit 302 has generated a high-voltage DC voltage under external control, the positive pole DC1+ of the high-voltage DC voltage is applied to the anode 9 of the gate-controlled X-ray tube, and at the same time, the negative pole DC1− of the high-voltage DC voltage is loaded to the cathode filament 7. At this time, the first switch unit 306-1 is turned off and the second switch unit 307-1 is turned on, forming an electrical path between the gate 8 and the negative pole DC4− of the third set of low-voltage DC voltages. The potential of the gate 8 is equal to the potential of the negative pole DC4− of the third set of low-voltage DC voltages, which is a lower potential than that of the negative pole DC1− of the high-voltage DC voltage. Since the cathode filament 7 is connected to the negative pole DC1− of the high-voltage DC voltage, the potential of the gate 8 is lower than the potential of the cathode filament 7. At this time, although the gate-controlled X-ray tube 308 has been loaded with the high-voltage DC voltage generated by the high-voltage DC power supply unit, and the cathode filament 7 has been heated to a sufficient temperature, since the gate 8 has a lower potential than that of the filament 7, electrons of the cathode filament 7 are suppressed and cannot be emitted, so that X-rays cannot be generated.

When the central information processing unit 309 receives an exposure instruction, under the control of the central information processing unit 309, the first switch unit 306-1 is turned on and the second switch unit 307-1 is turned off. At this time, an electrical path is formed between the gate 8 and the negative pole DC1− of the high-voltage DC voltage. The potential of the gate 8 is equal to the potential of the negative pole DC1− of the high-voltage DC voltage. Since the cathode filament 7 is also connected to the negative pole DC1− of the high-voltage DC voltage, the potential of the gate 8 is equal to the potential of the cathode filament 7. At this time, the electrons on the cathode filament 7 can reach the anode 9 of the X-ray tube 308 under high-voltage acceleration, and X-rays are generated.

When it is desired to terminate the X-rays, the first switch unit 306-1 is turned off and the second switch unit 307-1 is turned on, forming an electrical path between the gate 8 and the negative pole DC4− of the third set of low-voltage DC voltages. The potential of the gate 8 is equal to the potential of the negative pole DC4− of the third set of low-voltage DC voltages, which is a lower potential than that of the negative pole DC1− of the high-voltage DC voltage. Since the cathode filament 7 is connected to the negative pole DC1− of the high-voltage DC voltage, the potential of the gate 8 is lower than the potential of the cathode filament 7, so that the electrons of the cathode filament 7 are suppressed and X-ray emission is terminated.

Similarly, when the first switch unit 306-2 is turned on and the second switch unit 307-2 is turned off, the potential of the other gate 8 is equal to the potential of the other cathode filament 7. X-rays can be generated.

When the first switch unit 306-2 is turned off and the second switch unit 307-2 is turned on, the potential of the other gate 8 is lower than the potential of the other cathode filament 7. X-rays cannot be generated.

In the above three embodiments, each of the communication units may comprise a wireless communication module A, and the wireless communication module A is connected to the central information processing unit. A wireless communication module B paired with the wireless communication module A is connected to the external power supply and control unit outside the housing. The central information processing unit realizes parameter transferring and timing control with an external power supply and control unit outside the housing by means of the wireless communication module A and the wireless communication module B. In this case, instead of using an optical fiber, a wireless communication medium can be used to realize wireless transmission of information.

In the above three embodiments, two single-gate-controlled X-ray tubes or one dual-gate-controlled X-ray tube are/is used to realize dual-focus and dual-gate control. In other embodiments of the present invention, multiple single-gate-controlled X-ray tubes and/or dual-gate-controlled X-ray tubes can also be used to realize multi-focus alternate projection of the same target under multi-gate control, so as to obtain multiple (or multiple series of) images with parallax of the same object, thereby realizing acquisition and reconstruction of stereo X-ray images (including binocular stereo images). For multi-focus and multi-gate-controlled applications, the total number of gates of the X-ray tubes is equal to the number of focus points. By providing multiple first switch units and multiple second switch units to correspondingly control the gate voltage of each of the multiple gates, it is possible to control the emission and termination of multi-focus X-rays, thus constructing a three-dimensional X-ray image.

The X-ray machine head realized by the above three implementations needs to be matched with an X-ray acquisition apparatus, including but not limited to the use of a C-arm mechanical structure, a G-arm mechanical structure or other means, such that the X-ray machine head is positioned relative to an image intensifier, a flat panel detector or other X-ray acquisition apparatus to make sure that these acquisition apparatuses can successfully acquire the required X-rays when the X-ray machine head is controlled to emit X-rays, and then generate enough data to generate spatio-temporal models of substances in a space between the machine head and the acquisition apparatus. These models include, but not limited to, two-dimensional or three-dimensional images and related parameters.

It has been verified that in the above three embodiments, the volume of the X-ray machine head can be controlled within the range of 0.4 m*0.3 m*0.2 m, which can be conveniently applied to mobile devices.

In some embodiments of the present invention, the first switch unit and the second switch unit jointly constitute a high-speed and high-voltage electronic switch unit.

In some embodiments of the present invention, the central information processing unit may be a single-chip microcomputer, an ARM processor or a DSP chip, and can adjust the magnitudes of three sets of low-voltage DC voltages output by the low-voltage DC power supply unit by sending a control command to the low-voltage DC power supply unit.

In some embodiments of the present invention, the inside of the housing may be vacuum.

The present invention also provides an X-ray image device, which comprises the X-ray machine head in the above-mentioned embodiments.

The preferred and specific embodiments of the present invention have been described in detail above. It should be understood that a person of ordinary skill in the art would be able to make various modifications and variations according to the concept of the present invention without involving any inventive effort. Therefore, any technical solution that can be obtained by a person skilled in the art by means of logical analysis, reasoning or limited trials on the basis of the prior art and according to the concept of the present invention should fall within the scope of protection defined by the claims.

The invention claimed is:

1. An X-ray machine head, comprising:
a first DC power supply unit, a main module, and one or more X-ray tubes;
wherein the first DC power supply unit generates a high-voltage DC voltage; and a negative pole of the high-voltage DC voltage is directly connected to the main module, and is also directly connected to a cathode filament of each of the one or more X-ray tubes; and
wherein the main module is connected to a gate of each of the one or more X-ray tubes; and the main module is configured to provide a first voltage or a second voltage to the gate; wherein the potential of the first voltage is equal to the potential of the negative pole of the high-voltage DC voltage, and the potential of the second voltage is lower than the potential of the negative pole of the high-voltage DC voltage;
wherein the main module comprises a second DC power supply unit, one or more first switch units, one or more second switch units; wherein the second DC power supply unit is connected to the one or more first switch units and the one or more second switch units respectively; wherein the one or more first switch units provides one of the first voltage and the second voltage to the gate after the one or more first switch units are turned on, and the one or more second switch units provides the other of the first voltage and the second voltage to the gate after the one or more second switch units are turned on.

2. The X-ray machine head of claim 1, wherein the second DC power supply unit generates multiple sets of low-voltage DC voltage; wherein a positive pole of one of the multiple sets of low-voltage DC voltage is connected to an input end of each of the one or more first switch units, a negative pole of the one of the multiple sets of low-voltage DC voltage is connected an output end of each of the one or more second switch units; an output end of each of the one or more first switch units is correspondingly connected to an input end of each of the one or more second switch units.

3. The X-ray machine head of claim 2,
wherein the multiple sets of low-voltage DC voltage include: a first set of low-voltage DC voltage, a second set of low-voltage DC voltage and a third set of low-voltage DC voltage; wherein a negative pole of the first set of low-voltage DC voltage, a negative pole of the second set of low-voltage DC voltage, and a positive pole of the third set of low-voltage DC voltage are jointly connected to the negative pole of the high-voltage DC voltage; the positive pole of the third set of low-voltage DC voltage is also connected to the input end of each of the one or more first switch units; and a negative pole of the third set of low-voltage DC voltage is connected to the output end of each of the one or more second switch units.

4. The X-ray machine head of claim 3, wherein the main module further comprises a central information processing unit;
wherein the second DC power supply unit is connected to the central information processing unit; the one or more first switch units are all connected to the central information processing unit; the one or more second switch units are all connected to the central information processing unit;
wherein a positive pole of the second set of low-voltage DC voltage and the negative pole of the second set of low-voltage DC voltage are both connected to the central information processing unit; and
wherein the number of the first switch units is equal to the number of the second switch units, and is also equal to the number of gates of the one or more X-ray tubes.

5. The X-ray machine head of claim 4, further comprising: a housing, one or more filament power supply units, and a communication unit;
wherein the communication unit is connected to the central information processing unit,
wherein the first DC power supply unit, the second DC power supply unit, the one or more filament power supply units, the communication unit, the one or more first switch units, the one or more second switch units, the one or more X-ray tubes and the central information processing unit are all contained in the housing; and
wherein the first set of low-voltage DC voltage is connected to each of the one or more filament power supply units.

6. The X-ray machine head of claim 5, wherein the housing is filled with an insulating medium, and the insulating medium circulates in the housing.

7. The X-ray machine head of claim 6, wherein the X-ray tubes comprise single-gate-controlled X-ray tubes, and the number of the single-gate-controlled X-ray tubes is equal to the number of the first switch units.

8. The X-ray machine head of claim 7, wherein two ends of an output voltage of each of the one or more filament power supply units are correspondingly connected to two ends of the cathode filament of each of the single-gate-controlled X-ray tubes.

9. The X-ray machine head of claim 8, wherein a positive pole of the high-voltage DC voltage is connected to an anode of each of the single-gate-controlled X-ray tubes, and the negative pole of the high-voltage DC voltage is connected to either end of the cathode filament of each of the single-gate-controlled X-ray tubes.

10. The X-ray machine head of claim 6, wherein the X-ray tubes comprise dual-gate-controlled X-ray tubes, and the number of the dual-gate-controlled X-ray tubes is equal to half of the number of the first switch units.

11. The X-ray machine head of claim 10, wherein two ends of an output voltage of each of the one or more filament power supply units are correspondingly connected to two ends of each cathode filament of each of the dual-gate-controlled X-ray tubes.

12. The X-ray machine head of claim 11, wherein a positive pole of the high-voltage DC voltage is connected to an anode of each of the dual-gate-controlled X-ray tubes, and the negative pole of the high-voltage DC voltage is connected to either end of each cathode filament of each of the dual-gate-controlled X-ray tubes.

13. The X-ray machine head of claim 5, wherein each of the one or more filament power supply units has a signal input and feedback port, and all the signal inputs and feedback ports are connected to the central information processing unit.

14. The X-ray machine head of claim 5, wherein an external power supply and control unit is also provided outside the housing; and the external power supply and control unit is connected to the communication unit, the second DC power supply unit, and the first DC power supply unit.

15. The X-ray machine head of claim 14, wherein the communication unit is connected to the external power supply and control unit in a wired or wireless manner through a communication medium.

16. The X-ray machine head of claim 14, wherein a feedback signal end of the first DC power supply unit is connected to the external power supply and control unit.

17. An X-ray image device, comprising an X-ray machine head, wherein the X-ray machine head comprises:
   a first DC power supply unit, a main module, and one or more X-ray tubes;
   wherein the first DC power supply unit generates a high-voltage DC voltage; and a negative pole of the high-voltage DC voltage is directly connected to the main module, and is also directly connected to a cathode filament of each of the one or more X-ray tubes; and
   wherein the main module is connected to a gate of each of the one or more X-ray tubes; and the main module is configured to provide a first voltage or a second voltage to the gate;
   wherein the potential of the first voltage is equal to the potential of the negative pole of the high-voltage DC voltage, and the potential of the second voltage is lower than the potential of the negative pole of the high-voltage DC voltage;
   wherein the main module comprises a second DC power supply unit, one or more first switch units, one or more second switch units; wherein the second DC power supply unit is connected to the one or more first switch units and the one or more second switch units respectively; wherein the one or more first switch units provides one of the first voltage and the second voltage to the gate after the one or more first switch units are turned on, and the one or more second switch units provides the other of the first voltage and the second voltage to the gate after the one or more second switch units are turned on.

18. The X-ray image device of claim 17, wherein the second DC power supply unit generates multiple sets of low-voltage DC voltage; wherein a positive pole of one of the multiple sets of low-voltage DC voltage is connected to an input end of each of the one or more first switch units, a negative pole of the one of the multiple sets of low-voltage DC voltage is connected an output end of each of the one or more second switch units; an output end of each of the one or more first switch units is correspondingly connected to an input end of each of the one or more second switch units.

19. The X-ray image device of claim 18, wherein the main module further comprises a central information processing unit;
   wherein the second DC power supply unit is connected to the central information processing unit; the one or more first switch units are all connected to the central information processing unit; and the one or more second switch units are all connected to the central information processing unit;
   wherein the multiple sets of low-voltage DC voltage include: a first set of low-voltage DC voltage, a second set of low-voltage DC voltage and a third set of low-voltage DC voltage; wherein a negative pole of the first set of low-voltage DC voltage, a negative pole of the second set of low-voltage DC voltage, and a positive pole of the third set of low-voltage DC voltage are jointly connected to the negative pole of the high-voltage DC voltage; the positive pole of the third set of low-voltage DC voltage is also connected to the input end of each of the one or more first switch units; and a negative pole of the third set of low-voltage DC voltage is connected to the output end of each of the one or more second switch units;
   wherein a positive pole of the second set of low-voltage DC voltage and the negative pole of the second set of low-voltage DC voltage are both connected to the central information processing unit; and
   wherein the number of the first switch units is equal to the number of the second switch units, and is also equal to the number of gates of the one or more X-ray tubes.

20. The X-ray image device of claim 19, wherein the X-ray machine head further comprises: a housing, one or more filament power supply units, and a communication unit;
   wherein the first DC power supply unit, the second DC power supply unit, the one or more filament power supply units, the communication unit, the one or more first switch units, the one or more second switch units, the one or more X-ray tubes and the central information processing unit are all contained in the housing;
   wherein the first set of low-voltage DC voltage is connected to each of the one or more filament power supply units; and
   wherein the housing is filled with an insulating medium, and the insulating medium circulates in the housing.

* * * * *